United States Patent [19]

McAllister

[11] Plant 4,257

[45] May 30, 1978

[54] PLANT OF THE FERN FAMILY

[76] Inventor: Howard G. McAllister, 1100 NW. 75th Ave., Plantation, Fla. 33303

[21] Appl. No.: 795,394

[22] Filed: May 9, 1977

[51] Int. Cl.[2] ..... A01H 9/00
[52] U.S. Cl. ..... Plt./88
[58] Field of Search ..... Plt./88

*Primary Examiner*—Robert E. Bagwill
*Attorney, Agent, or Firm*—Roger L. Martin

[57] ABSTRACT

A new and distinct plant variety of the fern family that appeared as a vegetative mutation on a plant specimen of the *Nephrolepis exaltata* 'McAllister' variety and like its parent has a notable absence of sori. In comparison to the parent the fronds exhibit a more delicate texture that may be attributed to generally longer pinnae with pinnule margins that exhibit a predominance of pinnately lobed to pinnately divided lobing.

3 Drawing Figures

The invention relates to a new and distinct plant variety of the fern (Polypodiaceae) family and which has been named *Nephrolepis exaltata* 'Courtney Anne' by the inventor.

Plant varieties of the fern family commonly appear in the marketplace and many varieties have an unknown origin but which are nevertheless endowed with characteristics that provide greater or lesser appeal to the general purchasing public. One of the more popular varieties of the fern family is the so-called 'Curly Boston' variety of the *exaltata* species. Specimens of this variety have compound pinnate fronds that grow in a fairly compact rosette arrangement and which are endowed with numerous clusters of sporangia and these sori have been frequently mistakenly considered by the unenlightened purchasing public to be clusters of insect eggs. As is the case with the 'Curly Boston' variety, most varieties of the fern family have a sporophyte generation that is well endowed with sori that tend to darken in color and become more noticeable to the purchasing public as the fronds mature and age. The natural reluctance of the purchasing public to acquire plant life that is seemingly infested with insect producing eggs is understandable and one of the objectives of the invention has been to develop a new plant variety of the fern family which has an absence of sori in the frond structure.

The recently patented 'McAllister' variety of the *exaltata* species has an absence of sori in the frond structure and forms the subject matter of U.S. Plant Pat. No. 3,936. Specimens of the 'McAllister' variety are characterized by compound bipinnate fronds that have a noticeable absence of sori and which in comparison to the fronds of the 'Curly Boston' variety have a more robust appearance and more compact rosette arrangement. In comparison, they are also faster maturing and generally longer and wider in appearance at maturity than those of the 'Curly Boston' variety.

The new variety forming the subject matter of this application appeared as a vegetative mutation on a plant specimen of the *Nephrolepis exaltata* 'McAllister' variety which was under cultivation in a nursery at Ft. Lauderdale, Fla., and since the initial discovery of the new variety, has been asexually reproduced by the inventor at the Ft. Lauderdale nursery by the propagation of stem cuttings taken from the original plant specimen. Through successive propagations, it has been ascertained that the specimens of the new plant variety may be distinguished from those of its parent variety and from other related varieties known to the inventor by a growth habit which provides specimens with compound bipinnate fronds which grow in a compact rosette arrangement with a notable absence of sori and which in comparison to specimens of the parent variety exhibit an overall finer or more delicate texture that is attributed to slightly longer pinnae with pinnule margins that exhibit a predominance of pinnately lobed to pinnately divided lobing.

The accompanying drawings serve, by color photographic means, to illustrate the new variety and wherein one color photograph shows a 5 month old specimen of the variety which had been grown under nursery conditions in a plastic container, yet another photograph shows ventral and dorsal surfaces of separate fronds, and a third color photograph is a close up view of a portion of the plant seen in the first mentioned photograph and which illustrates the appearingly delicate texture of the fronds.

The following is a detailed description of the new plant variety with colors and hues, unless otherwise clearly indicated by the text, being named in accord with the ISCC-NBS Method of Designating Colors (U.S. Department of Commerce, National Bureau of Standards, Circular 553, issued Nov. 1, 1955), the named colors being interpreted from color notations derived by comparison with the color specimens in the current "Neighboring Hues Edition" of the Munsell Book of Color, published by the Munsell Color Company, Inc., of Baltimore, Md.

PLANT DESCRIPTION

Name: *Nephrolepis exaltata* 'Courtney Anne'

Parentage: A vegetative mutation from *Nephrolepis exaltata* 'McAllister'.

Classification:

*Botanic.*—1. Family: Polypodiaceae (Fern Family). 2. Genus: Nephrolepis. 3. Species: *exaltata.*

*Commercial.*—Foliage plant.

Sporophyte Generation (Common Reference):

*Form.*—Terrestrial, herbaceous, shade loving rosette of erect young and arching to drooping mature fronds.

*Stems.*—1. General: Rhizomatous and stoloniferous with an advantitious root system. 2. Stolons (rhizomes — common reference): (a) General — Herbaceous and branched. (b) Texture — Generally villous with sparse to moderate coverage of elongated membranous hairs that expand toward the insertion and are commonly between 1 mm. and 5 mm. in length and with a texture being cespitose at the apices of primary and secondary stolons. (c) Shape — Generally cylindrical. (d) Size — (1) Diameter: Usually between 0.2 and 1.8 mm. (2) Length: Indeterminate. (e) Color — Commonly light yellow green (near 5 GY 8/6), moderate yellow green (2.5 GY 7/6) (5 GY 7/6) (5 GY 6/6), strong yellow green (2.5 GY 7/8) (2.5 GY 6/8) (5 GY 7/8) (near 5 GY 6/8) and/or brilliant yellow green (2.5 GY 8/8).

*Fronds.*—1. General: Exstipulate, bipinnately compound and foliaceous with circinate venation and a notable absence of sori, and with a rachis bearing a compact arrangement of pinnae. 2. Arrangement: Rosette. 3. Shape: Generally varies from obcuneate to broadly lanceolate. 4. Size: (a) Length (including stipe) — Usually between 40 cm. and 79 cm. (b) Width (maximum) — Usually between 20 cm. and 48 cm. 5. Stipe: (a) General — Herbaceous and fleshy at early maturity and becoming dry and brittle with age. (b) Texture — Generally villous with the hairs being elongated, membranous and expanding toward the insertion and with the concentration of hairs being heaviest at the basal insertion and decreasing distally thereof. (c) Shape — Generally cylindrical with an expanded basal attachment and an adaxial surface depression or groove which begins distally of the basal insertion and becomes most prominent at mergence with the rachis. (d) Size — (1) Length: Usually between 6 cm. and 15 cm. when measured from insertion to most basally located pinna emergence at full maturity. (2) Diameter: Usually between 1.5 mm. and 3 mm. intermediate insertion and basally located pinna emergence at full maturity. (e) Color — (1) Abaxial surface: Commonly moderate reddish brown (7.5 R 3/4) (near 10 R 3/6) (10 R 3/4) (near 2.5 YR 4/4), moderate brown (5 YR 4/4) and/or strong brown (2.5 YR 4/6) (5 YR 4/6). (2) Adaxial surface: Commonly light olive (5 Y 5/6) (near 5 Y 5/4) (near 7.5 Y 5/6) (near 7.5 Y 5/4) (near 10 Y 6/4) (near 10 Y 5/6), dark greenish yellow (near 10 Y 6/6) and/or moderate yellow green (2.5 GY 6/6) (2.5 GY 6/4) (5 GY 6/6) (near 5 GY 5/6) (near 5 GY 5/4). 6. Rachis: (a) General — Herbaceous and generally flexible and fleshy during early maturity and hardening with age. (b) Texture — Villous at maturity with a moderate concentration of hairs that are elongated, membranous and expanding toward the insertion. (c) Shape — Generally cylindrical with an axially extending adaxial surface depression or groove that merges with that of the stipe. (d) Size — (1) Length (between apex and basal pinna emergence): Usually between 29 cm. and 66 cm. at full maturity. (2) Diameter (intermediate apex and basal pinna emergence): Usually between 1 mm. and 3 mm. at full maturity. (e) Color — (1) General: Distal end surface color dominated by olive, greenish yellow and/or yellow green hues with proximal end abaxial surface color being dominated by brown and/or reddish brown hues that extend distally to mergence with distal end surface color. (2) Apexes: Commonly light olive (7.5 Y 5.6) (near 7.5 Y 5/4) (near 10 Y 5/6), dark greenish yellow (near 10 Y 6/6) and/or moderate yellow green (2.5 GY 6/6) (2.5 GY 5/6) (near 2.5 GY 5/4) (near 5 GY 6/6) (near 5 GY 6/4) (5 GY 5/6) (5 GY 5/4) (near 7.5 GY 5/4). (3) Abaxial surface: Commonly moderate reddish brown (7.5 R 3/4) (near 10 R 3/6) (10 R 3/4) (near 2.5 YR 4/4), moderate brown (5 YR 4/4) and/or strong brown (2.5 YR 4/6) (5 YR 4/6) at proximal end and merging distally with apex color. (4) Adaxial surface: Commonly light olive (5 Y 5/6) (near 5 Y 5/4) (near 7.5 Y 5/6) (near 7.5 Y 5/4) (near 10 Y 6/4) (near 10 Y 5/6), dark greenish yellow (near 10 Y 6/6) and/or moderate yellow green (2.5 GY 6/6) (2.5 GY 6/4) (5 GY 6/6) (near 5 GY 5/6) (near 5 GY 5/4) at proximal end and merging distally with apex color. 7. Pinnae: (a) General — Sessile, foliaceous with primary rachilla bearing a compact arrangement of pinnules. (b) Arrangement — Predominately alternate with occasional opposite arrangement at proximal end of rachis. (c) Shape — Commonly lanceolate with inequilateral pinnae being commonly present. (d) Size — (1) Length: Majority on fronds are usually between 4 mm. and 260 mm. (2) Width (maximum): Usually less than 9 cm. for longest pinna on rachis. (e) Primary Rachilla — (1) General: Herbaceous and flexible. (2) Texture: Generally villous with hairs being sparsely concentrated on lower surface, moderately concentrated on upper surface and moderately to heavily concentrated at the secondary rachilla insertions. (3) Orientation: Acute angle between axis of primary rachilla and rachis portion distally of rachilla insertion and with the rachilla axis being flexible and curved by gravity. (4) Shape: Elongated and oval in cross section with major axis generally normal to the general plane of primary and secondary rachilla and with a longitudinally extending depression or groove in the dorsal (upper) surface. (5) Spacing: Usually between 2 mm. and 25 mm. between primary rachilla on same side of rachis. (6) Size: (a) Length — Usually between 0.4 cm. and 26 cm. on majority of mature fronds. (b) Diameter — Usually between 0.1 mm. and 1 mm. intermediate insertion and apex on mature fronds. (7) Color: Commonly moderate yellow green (2.5 GY 7/6) (near 5 GY 7/6) (near 2.5 GY 6/6) (5 GY 6/6). (f) Pinnules — (1) General: Simple, sessile and herbaceous with variable pinnate lobing. (2) Texture: Sometimes glabrous but commonly very slightly pubescent on lower and upper surfaces. (3) Arrangement: Usually alternate with some opposite tendencies at insertion of primary rachilla. (4) Shape: Variable but generally lanceolate to oblanceolate with rhombic tendencies. (5) Margins: Irregular and variable with generally crenate lobed margins providing a predominance of pinnately lobed to pinnately divided distally projecting lobing in which the pinnately divided lobing is usually most pronounced in the area intermediate the insertion and apex of the secondary rachilla. (6) Size: (a) Length: Usually between 3 mm. and 51 mm. (b) Width (maximum) — Usually less than 19 mm. (7) Color: Upper and lower epidermis are commonly moderate yellow green (near 5

GY 7/6) (near 5 GY 6/6) (near 5 GY 5/6) (7.5 GY 5/6) (near 7.5 GY 5/4) and/or strong yellow green (5 GY 7/8). (8) Sori: None. (9) Secondary Rachilla: (a) General — Herbaceous, flexible and fleshy. (b) Texture — Generally slightly pubescent to glabrous. (c) Orientation — Usually ranging from perpendicular to primary rachilla to an acute angle between primary rachilla portion distally of secondary rachilla insertion. (d) Spacing — Usually between 1 mm. and 12 mm. for pinnules on same side of primary rachilla. (e) Shape — Elongated with an indentation or groove on the side opposite grooved portion of primary rachilla. (f) Size — (1) Length — Majority of mature pinnule are usually between 3 mm. and 51 mm. (2) Diameter: Usually less than 1.0 mm.

Gametophyte: None.

The above description is based on observations made during the month of January of well fertilized plants about 5 months old (from initial propagation) and which were grown under 60% shaded conditions in the Ft. Lauderdale, Fla., area.

The following is a general description of a plant specimen of the new variety which was propagated and grown under the above nursery conditions, the description being taken in the month of January.

General:

*Plant age (from initial propagation).*—5 months.

*Soil.*—Sterile peat moss housed in 10 inch (industrial classification) plastic container.

Stems:

*Stolons.*—1. Number: 23 primary. 2. Diameter: 1.2 mm. (average) 3. Branches per primary stolon: 7.1 (average). 4. Color: Moderate yellow green (2.5 GY 7/6) (5 GY 7/6) and strong yellow green (2.5 GY 7/8) (5 GY 7/8).

Fronds:

*General.*—1. Number of mature fronds: Nine. 2. Number of immature fronds: Five. 3. Number of senescent fronds: Seven.

*Size.*—1. Length (including stipe): From 40.6 cm. to 63.5 cm. and averaging 53.34 cm. 2. Width (maximum): From 26.5 cm. to 45.6 cm. and averaging 34.3 cm.

*Stipe.*—1. Length: 9.5 cm. (average). 2. Diameter: 2.6 mm. (average). 3. Color: (a) Abaxial surface — moderate reddish brown (near 2.5 YR 4/4), moderate brown (5 YR 4/4) and strong brown (2.5 YR 4/6) (5 YR 4/6). (b) Adaxial surface — moderate yellow green (near 2.5 GY 6/6) (5 GY 6/6) (near 5 GY 5/6) (5 GY 5/4).

*Rachis.*—1. Length: From 30.4 cm. to 54.5 cm. and averaging 43.82 cm. 2. Diameter: 2.1 mm. (average). 3. Color: (a) Apexes — light olive (near 7.5 Y 5/4) (7.5 Y 5/6), dark greenish yellow (near 10 Y 6/6) and moderate yellow green (near 5 GY 6/4) (5 GY 5/4). (b) Abaxial surface — moderate reddish brown (near 2.5 YR 4/4), moderate brown (5 YR 4/4) and strong brown (2.5 YR 4/6) (5 YR 4/6) and merging distally with the apex color. (c) Adaxial surface — light olive (near 7.5 Y 5/4) (7.5 Y 5/6), dark greenish yellow (near 10 Y 6/6) and moderate yellow green (near 5 GY 6/4) (5 GY 5/4) and merging distally with apex color.

*Pinnae.*—1. Size: (a) Length — Between 9 mm. and 210 mm. excepting diminutive pinnae in apex area. (b) Width (maximum) — 6.4 cm. (average) excepting diminutive pinnae in apex area. 2. Primary rachilla: (a) Length — Between 9 mm. and 210 mm. excepting diminutive pinnae in apex area. (b) Diameter — 0.6 mm. (average) excepting diminutive pinnae in apex area. 3. Pinnules: (a) Length (maximum) — 23 mm. (average). (b) Width (maximum) — 7.2 mm. (average). (c) Color — moderate yellow green (7.5 GY 5/6) (near 7.5 GY 5/4).

I claim:

1. The new and distinct plant variety of the fern family substantially as herein described and illustrated and characterized by a growth habit which provides specimens that have compound bipinnate fronds that grow in a compact rosette arrangement with a noticeable absence of sori, and which, in comparison to specimens of the parent variety, exhibit a more delicate texture that may be attributed to generally longer pinnae with pinnule margins that exhibit a predominance of pinnately lobed to pinnately divided lobing.

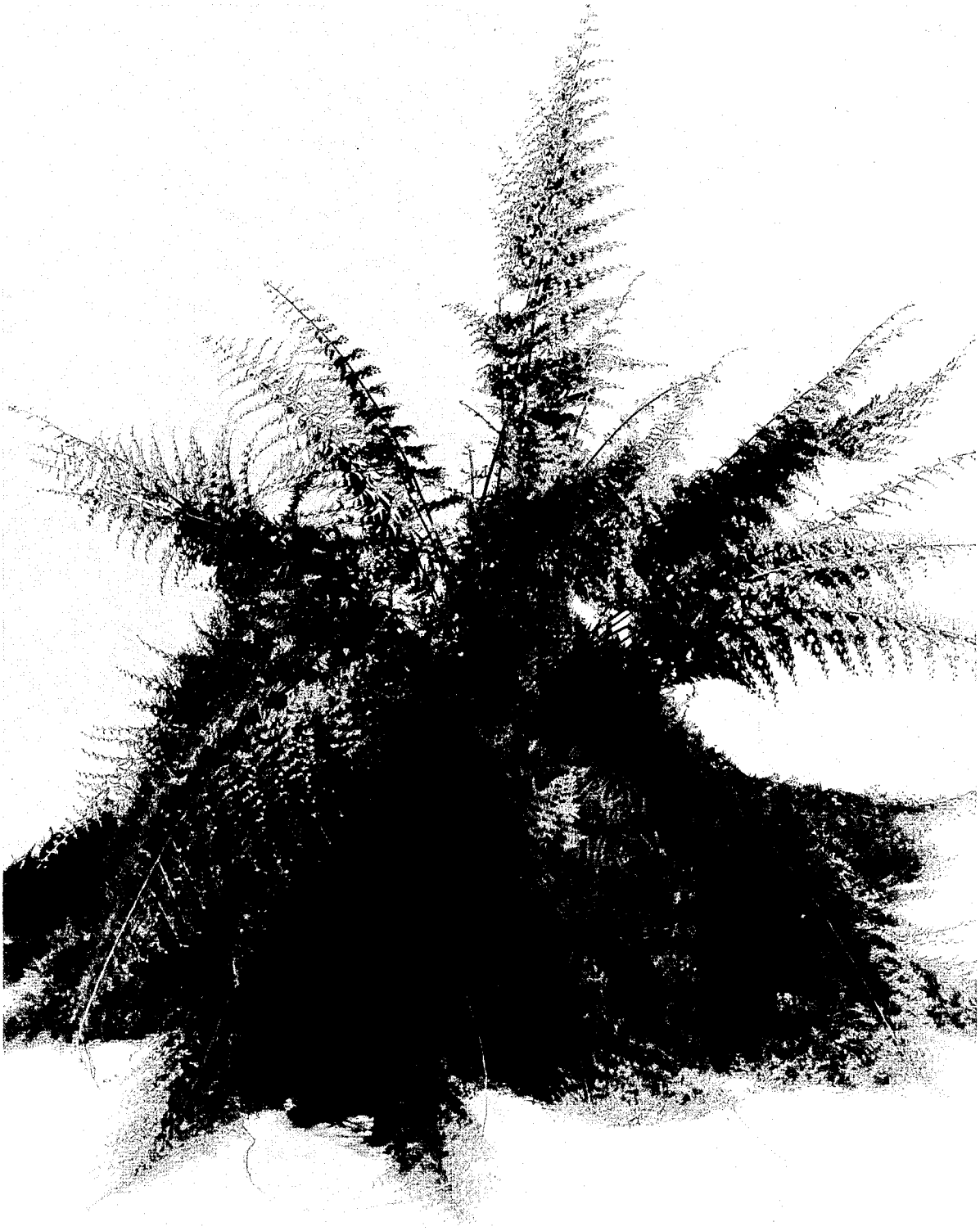

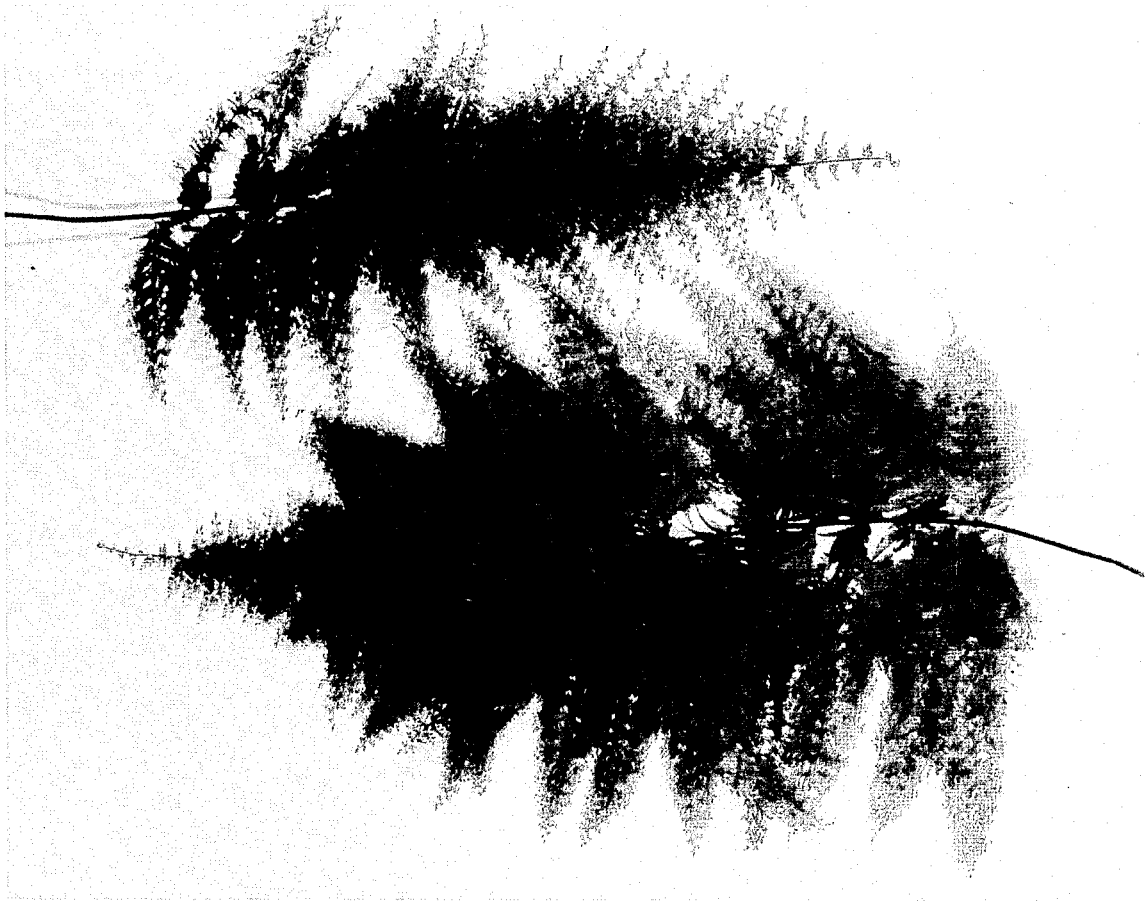
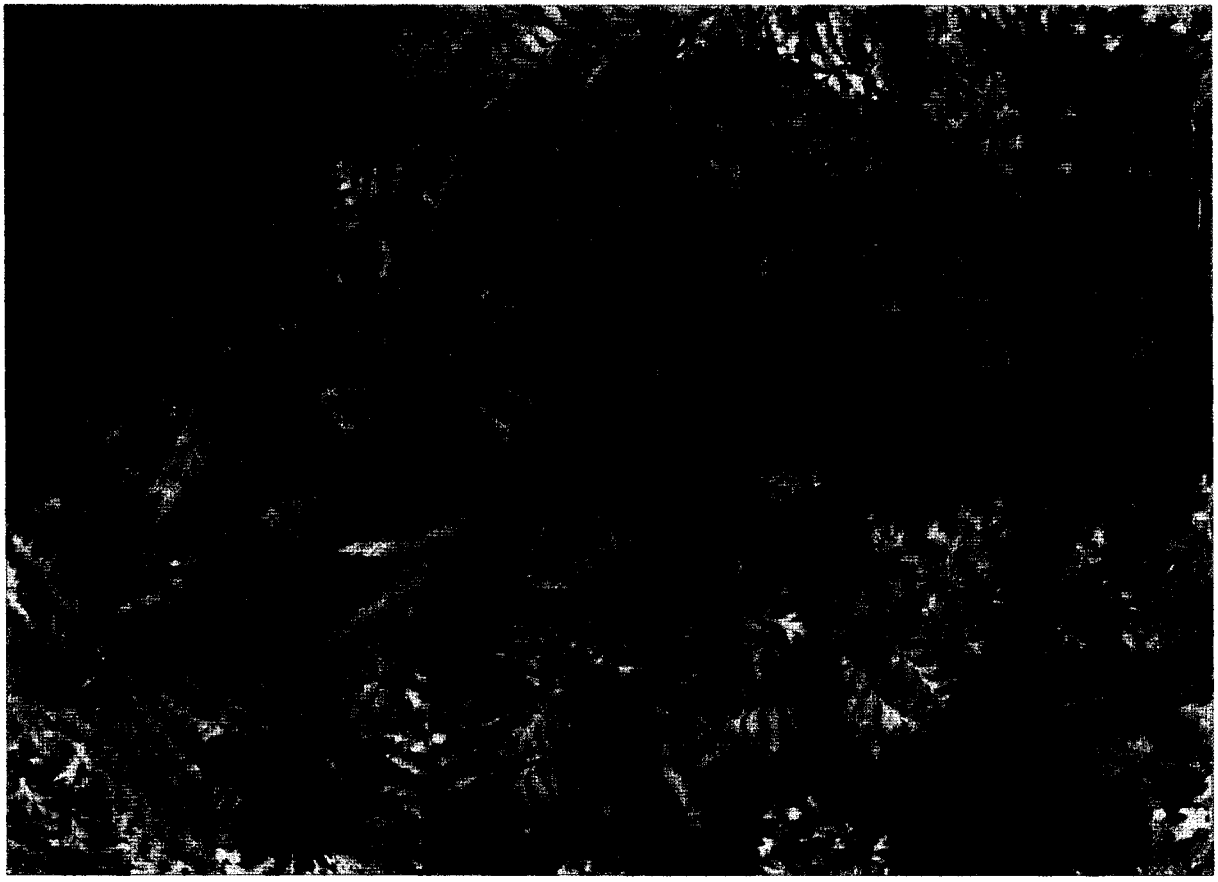

* * * * *